United States Patent [19]

Mookherjee et al.

[11] 4,157,351
[45] Jun. 5, 1979

[54] 1-(2,6,6-TRIMETHYL-1,3-CYCLOHEXADIEN-1-YL)-1,3-BUTANEDIONE AND ORGANOLEPTIC USES THEREOF

[75] Inventors: Braja D. Mookherjee, Holmdel; Richard A. Wilson, Westfield; Frederick L. Schmitt, Holmdel; Joaquin F. Vinals, Red Bank, all of N.J.; Jacob Kiwala, Brooklyn, N.Y.

[73] Assignee: International Flavors & Fragrances Inc., New York, N.Y.

[21] Appl. No.: 887,630

[22] Filed: Mar. 17, 1978

[51] Int. Cl.$^2$ ............................................. C07C 49/61
[52] U.S. Cl. ............................. 260/586 R; 131/17 R; 252/89 R; 252/132; 252/522; 424/596; 424/63; 424/65; 424/69; 424/70; 424/76; 426/650
[58] Field of Search ................................... 260/586 R

[56] References Cited

U.S. PATENT DOCUMENTS

| 3,923,896 | 12/1975 | Schulte-Elte | 260/586 R |
| 3,968,161 | 7/1976 | Schulte-Elte | 260/586 R |

OTHER PUBLICATIONS

Schulte-Elte et al., "Helv. Chem. Acta", vol. 56, Fasc. 1 (1973), p. 310.

*Primary Examiner*—Norman Morgenstern

*Attorney, Agent, or Firm*—Arthur L. Liberman; Franklin D. Wolffe

[57] ABSTRACT

Processes and compositions are described for the use in tobacco flavor and aroma and perfume aroma augmenting, modifying, enhancing and imparting compositions and as tobacco, perfume, cologne and perfumed article aroma imparting materials of 1-(2,6,6-trimethyl-1,3-cyclohexadien-1-yl)-1,3-butanedione which has the structure:

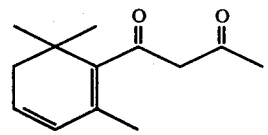

which also, in its enolate form, has the structure:

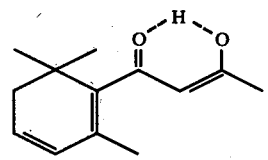

2 Claims, 7 Drawing Figures

I.R. SPECTRUM FOR EXAMPLE I

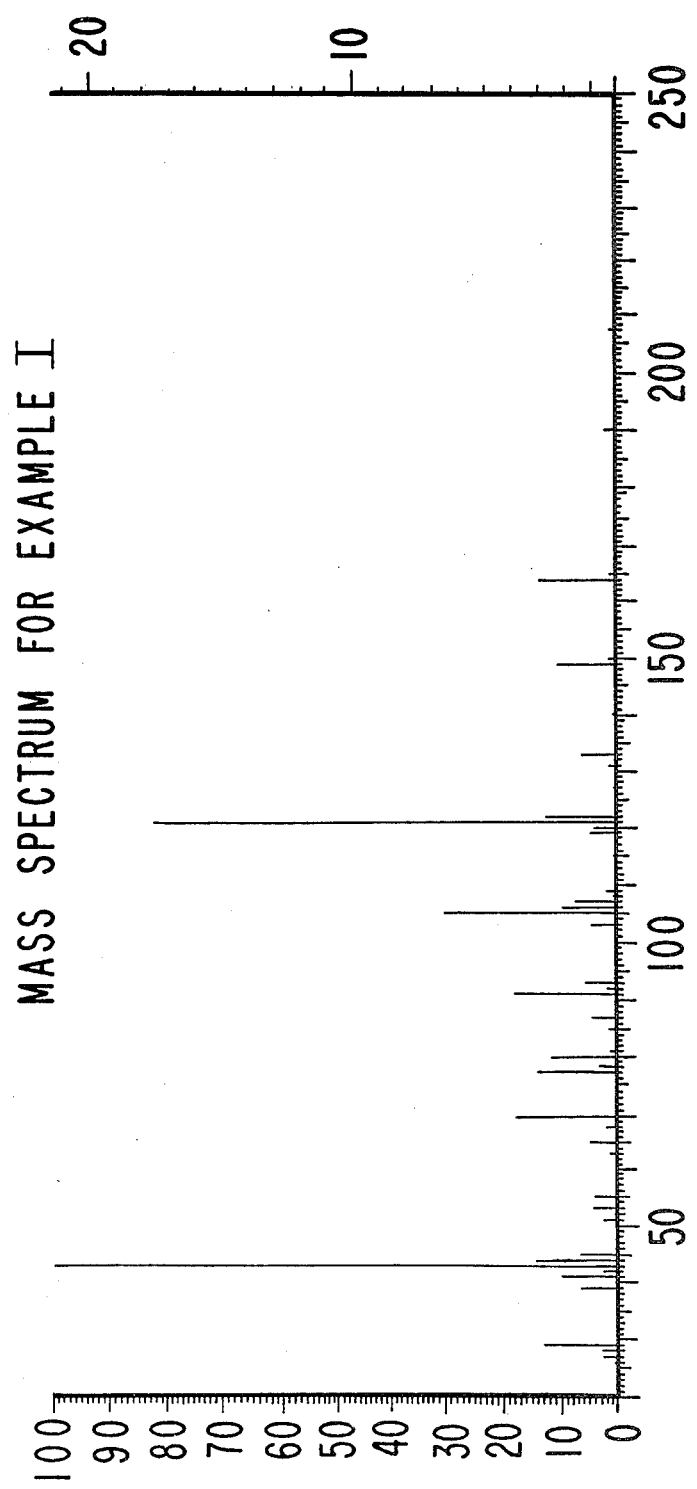
FIG.3 MASS SPECTRUM FOR EXAMPLE I

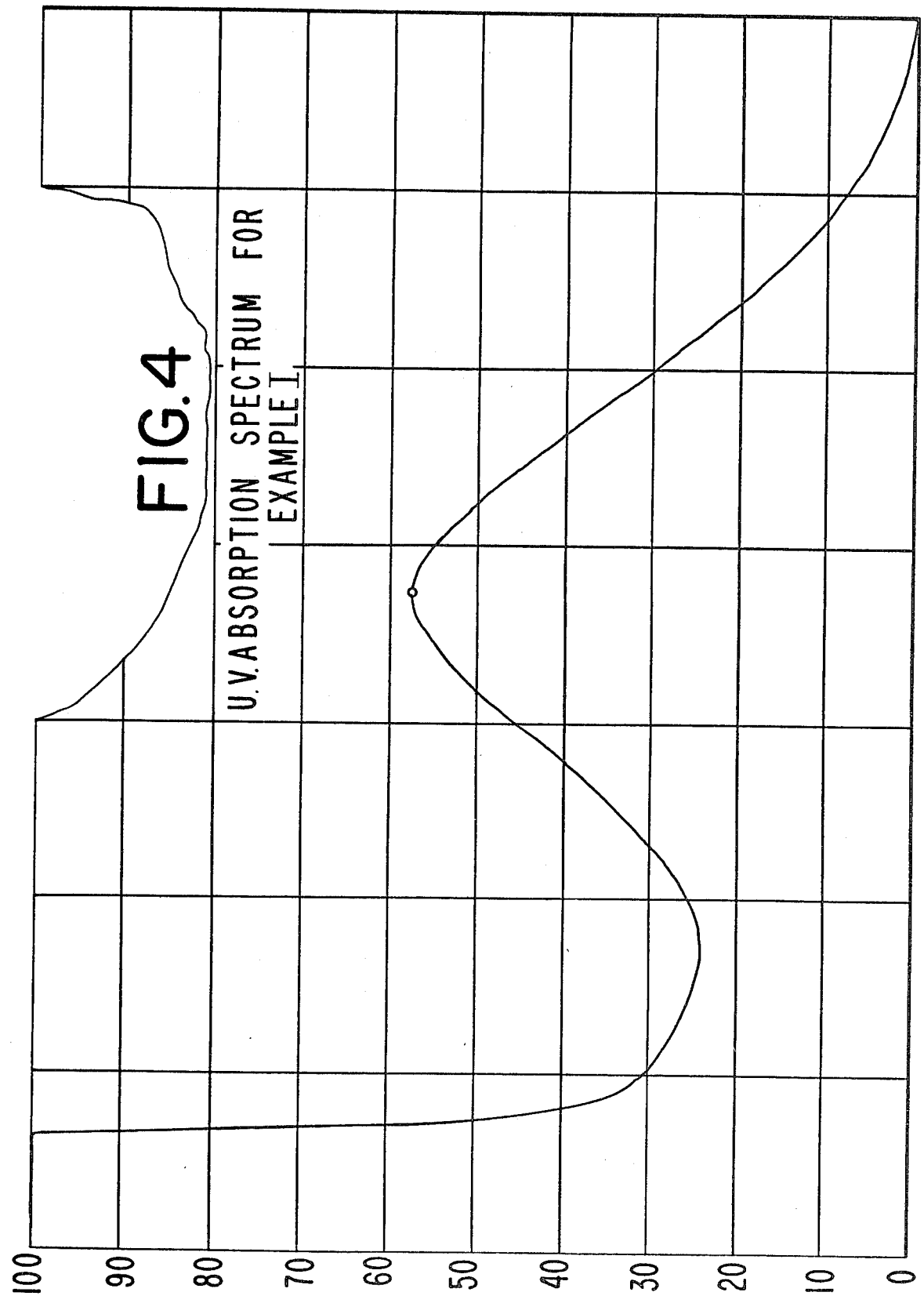

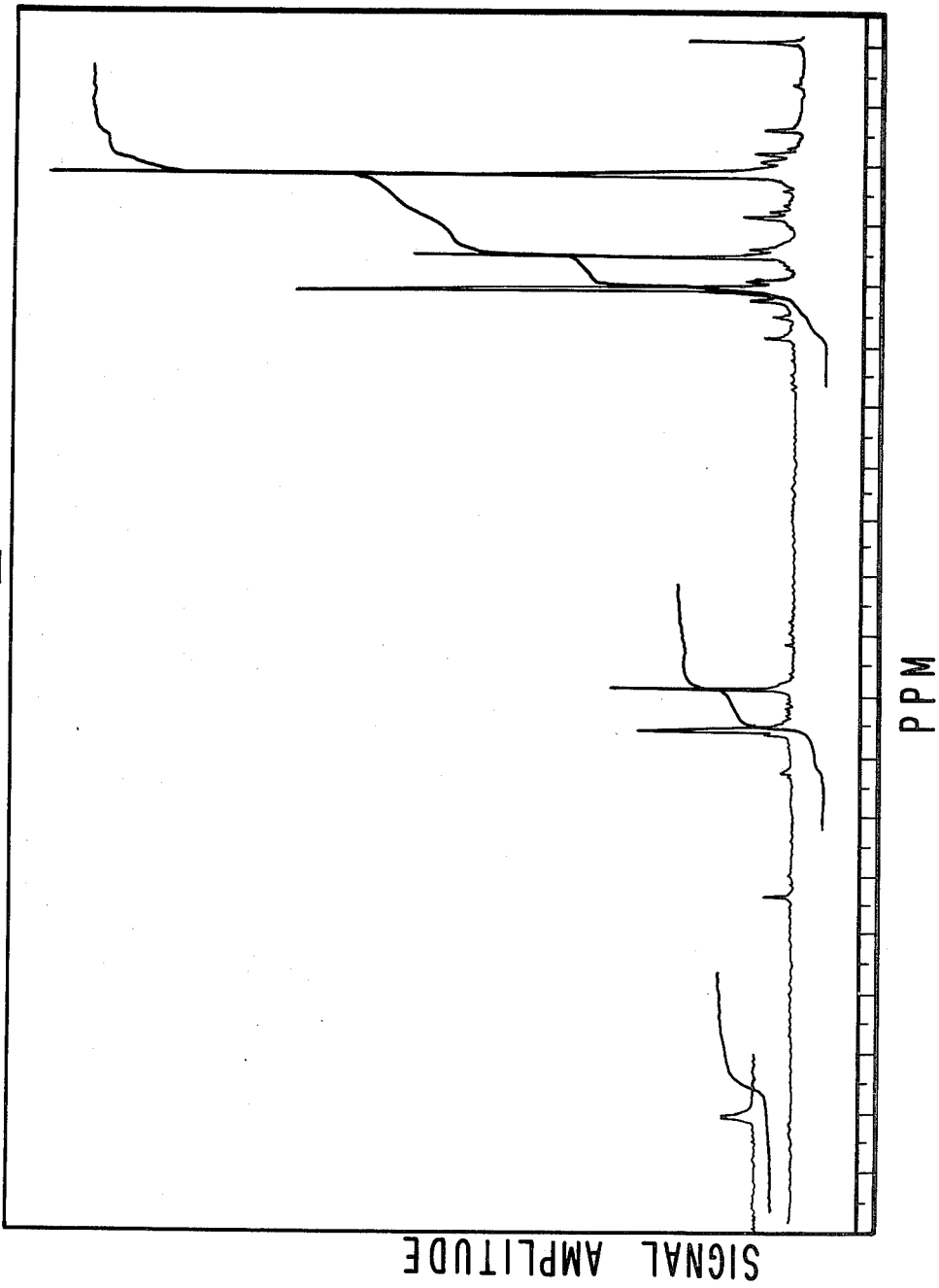

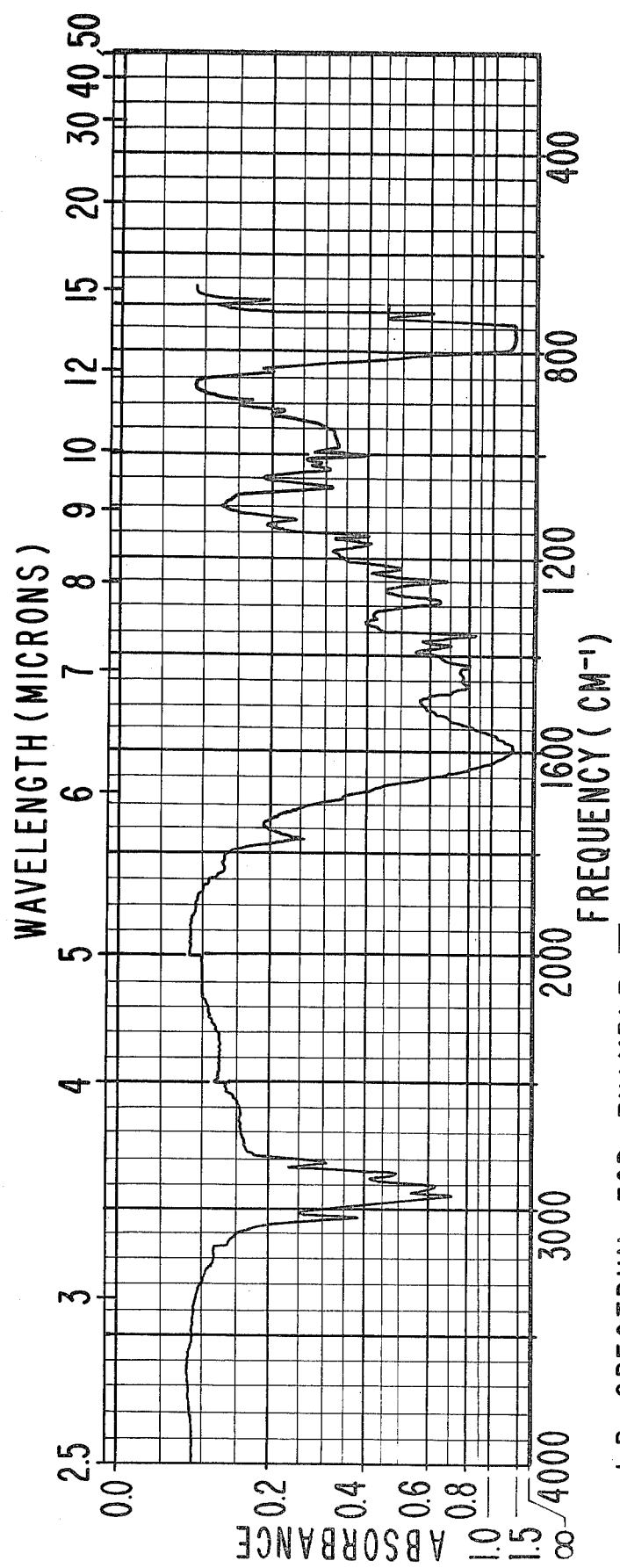
FIG. 6 IR SPECTRUM FOR EXAMPLE II

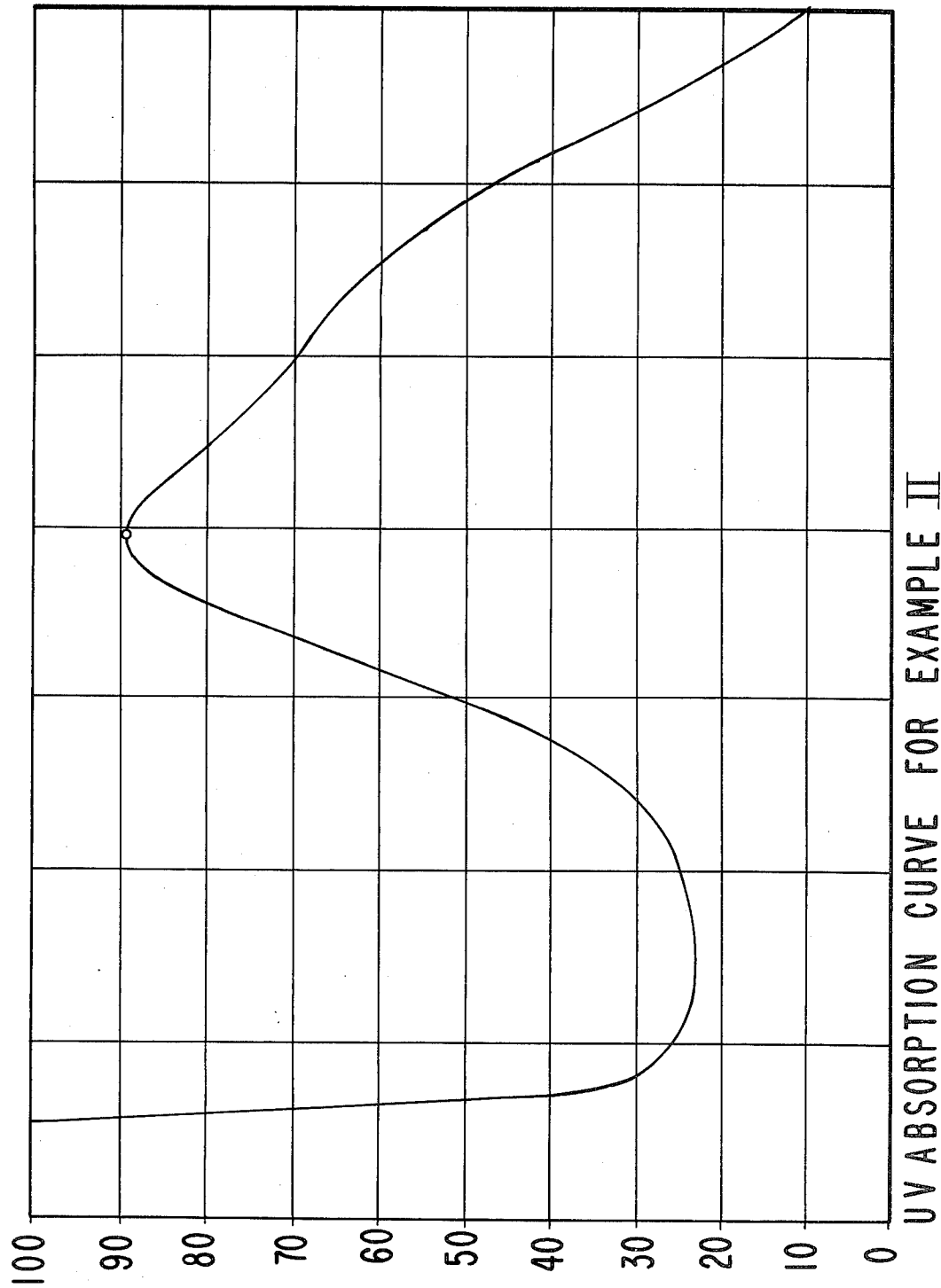

1-(2,6,6-TRIMETHYL-1,3-CYCLOHEXADIEN-1-YL)-1,3-BUTANEDIONE AND ORGANOLEPTIC USES THEREOF

BACKGROUND OF THE INVENTION

The present invention relates to 1-(2,6,6-trimethyl-1,3-cyclohexadien-1-yl)-1,3-butanedione produced by a novel process as set forth herein and as set forth and claimed in application for U.S. Patent Ser. No. 887,628 filed on even date herewith, and novel compositions using such 1-(2,6,6-trimethyl-1,3-cyclohexadien-1-yl)-1,3-butanedione to augment, alter, modify or enhance the flavor and/or aroma of consumable materials, or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product. Sweet, honey-like, fruity, grape-like, rose-like, ionone-like, hay-like and floral aromas with sea-amber or ambergris-like undertones and sweet-floral topnotes are desirable in several types of perfume compositions, perfumed articles and colognes.

Sweet, fruity, berry-like, fresh squeezed fruit (apple and grape) juice-like, hay-like and tea-like aromas prior to smoking and sweet, hay/tea aroma characteristics in the mainstream on smoking and sweet, tobacco-like and "fresh cigarette pack" aromas in the sidestream on smoking are particularly desirable in tobaccos and in tobacco flavoring compositions.

Compounds similar to 1-(2,6,6-trimethyl-1,3-cyclohexadien-1-yl)-1,3-butanedione having the structure:

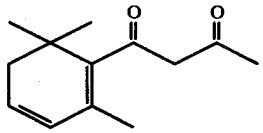

have been reported in the literature, but their uses for their organoleptic properties have not been reported nor are such uses implied. Thus, the diketones having the structures:

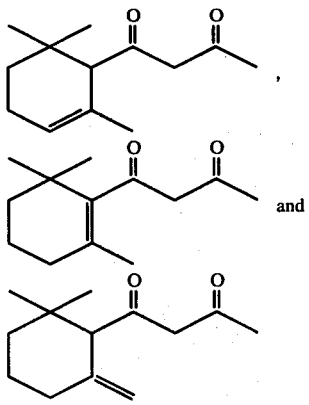

or their corresponding enolates having the generic structure:

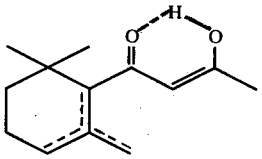

wherein a double bond could be situated at the $\Delta^1$ or $\Delta^2$ positions in the ring, or at the methylene group exocyclic to the ring, are reported by Schulte-Elte, Muller and Ohloff at Helv. Chim. Acta, Vol. 56, FASC 1 (1973) page 310 [Title: "Synthetische Ubergange von der Jonon- in die Damasconreihe"]. These compounds are, however, indicated to be useful as intermediates in synthesizing compounds of the "Damascone" series having the generic structure:

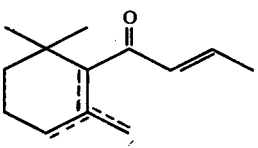

wherein one of the dashed lines is a pi double bond and each of the other dashed lines represents single bonds, and, individually, the structures:

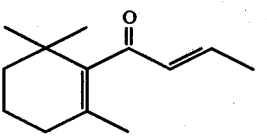

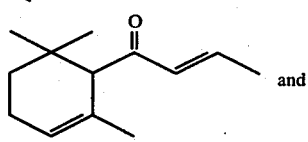 and

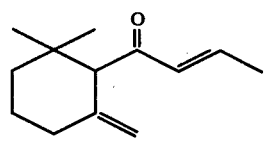

which are, in turn, useful for their organoleptic properties. However, the organoleptic properties of the members of the "Damascone" series are different in kind from the organoleptic properties of 1-(2,6,6-trimethyl-1,3-cyclohexadien-1-yl)-1,3-butanedione.

Schulte-Elte, U.K. Patent specification No. 1,391,736 discloses and claims a genus of compounds which includes 1-(2,6,6-trimethyl-1,3-cyclohexadien-1-yl)-1,3-butanedione and uses of the genus members, in general, for the organoleptic properties of the members of the genus, in general; but Schulte-Elte, U.K. Patent specification No. 1,391,736 does not specifically teach any specific cyclohexadiene compounds per se or their uses for their organoleptic propertues. Thus, U.K. Patent specification No. 1,391,736 states:

"The compounds to which the invention relates have the formula

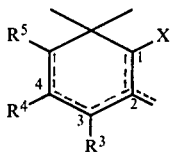

wherein:
X represents the group:

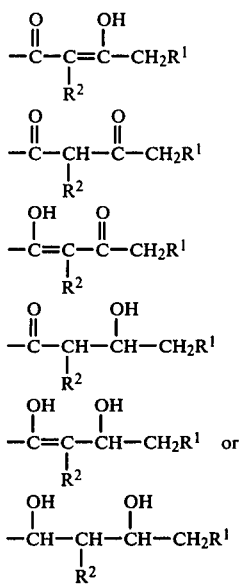

$R^1$, $R^2$, $R^3$, $R^4$ and $R^5$ may be the same or different, and each represents a hydrogen atom or a lower alkyl group having from 1 to 6 carbon atoms; and the ring is saturated or contains one endocyclic double bond in position 1, 2, 3 or 4, or an exocyclic double bond in position 2, or two conjugated double bonds in positions 1 and 3 ...

The new compounds of formula (I) include the following specific examples:

2,6,6-trimethyl-1-(1,3-dioxo-but-1-yl)-cyclohex-1-ene;
2-methylene-6,6-dimethyl-1-(1,3-dioxo-but-1-yl)-cyclohexane;
2,6,6-trimethyl-1-(3-hydroxy-butan-1-oyl)-cyclohex-1-ene;
2,6,6-trimethyl-1-(3-hydroxy-butan-1-oyl)-cyclohex-2-ene;
2,6,6-trimethyl-1-(2-methyl-1,3-dioxo-but-1-yl)-cyclohex-1-ene;
2,6,6-trimethyl-1-(2-methyl-1,3-dioxo-but-1-yl)-cyclohex-2-ene;
2-methylene-6,6-dimethyl-1-(2-methyl-1,3-dioxo-but-1-yl)-cyclohexane;
2,6,6-trimethyl-1-(2-methyl-3-hydroxy-butan-1-oyl)-cyclohex-2-ene;
2-methylene-6,6-dimethyl-1-(2-methyl-3-hydroxy-butan-1-oyl)-cyclohexane;
2,6,6-trimethyl-1-(2-methyl-1,3-dihydroxy-but-1-yl)-cyclohex-2-ene;
2,6,6-trimethyl-1-(2-methyl-1,3-dihydroxy-but-1-yl)-cyclohex-1-ene;
2,6,6-trimethyl-1-(1,3-dioxo-but-1-yl)-cyclohexane;
2,6,6-trimethyl-1-(1,3-dihydroxy-but-1-yl)-cyclohexane;
2,6,6-trimethyl-1-(1,3-dihydroxy-but-1-yl)-cyclohex-2-ene; and
2,6,6-trimethyl-1-(1,3-dihydroxy-but-1-yl)-cyclohex-1-ene."

None of the exemplified compounds of U.K. Patent specification No. 1,391,736 has a chemical structure which can be considered by one having ordinary skill in the art to be even remotely similar to 1-(2,6,6-trimethyl-1,3-cyclohexadien-1-yl)-1,3-butanedione.

In addition, the diketone having the structure:

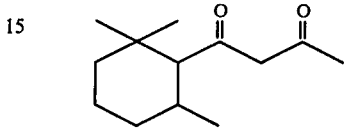

is indicated to be useful as a chemical intermediate at Helv. Chim. Acta 31, 2135–42 (1948) [V. Prelog and Frick, "Uber einige Oxo-tetrahydro-jonone"].

The diketone 1-(2,6,6-trimethyl-1,3-cyclohexadien-1-yl)-1,3-butanedione of the instant invention has properties different in kind from the diketones of the prior art.

BRIEF DESCRIPTION OF THE DRAWINGS

FIG. 3 is the mass spectrum (MS) for 3-hydroxy-1-(2,6,6-trimethyl-1,3-cyclohexadien-1-yl)-1-butanone produced according to Example IA.

FIG. 4 is the ultraviolet (UV) absorption spectrum for 3-hydroxy-1-(2,6,6-trimethyl-1,3-cyclohexadien-1-yl)-1-butanone produced according to Example IA, using a methanol solvent.

FIG. 5 is the NMR spectrum for 1-(2,6,6-trimethyl-1,3-cyclohexadien-1-yl)-1,3-butanedione produced according to Example II.

FIG. 6 is the infrared spectrum for 1-(2,6,6-trimethyl-1,3-cyclohexadien-1-yl)-1,3-butanedione produced according to Example II.

FIG. 7 is the UV absorption curve [$E_{1\,cm}1\% = 473.04$; Lamda$_{max} = 284$ nm] for 1-(2,6,6-trimethyl-1,3-cyclohexadien-1-yl)-1,3-butanedione produced according to Example II.

THE INVENTION

Figure 1:
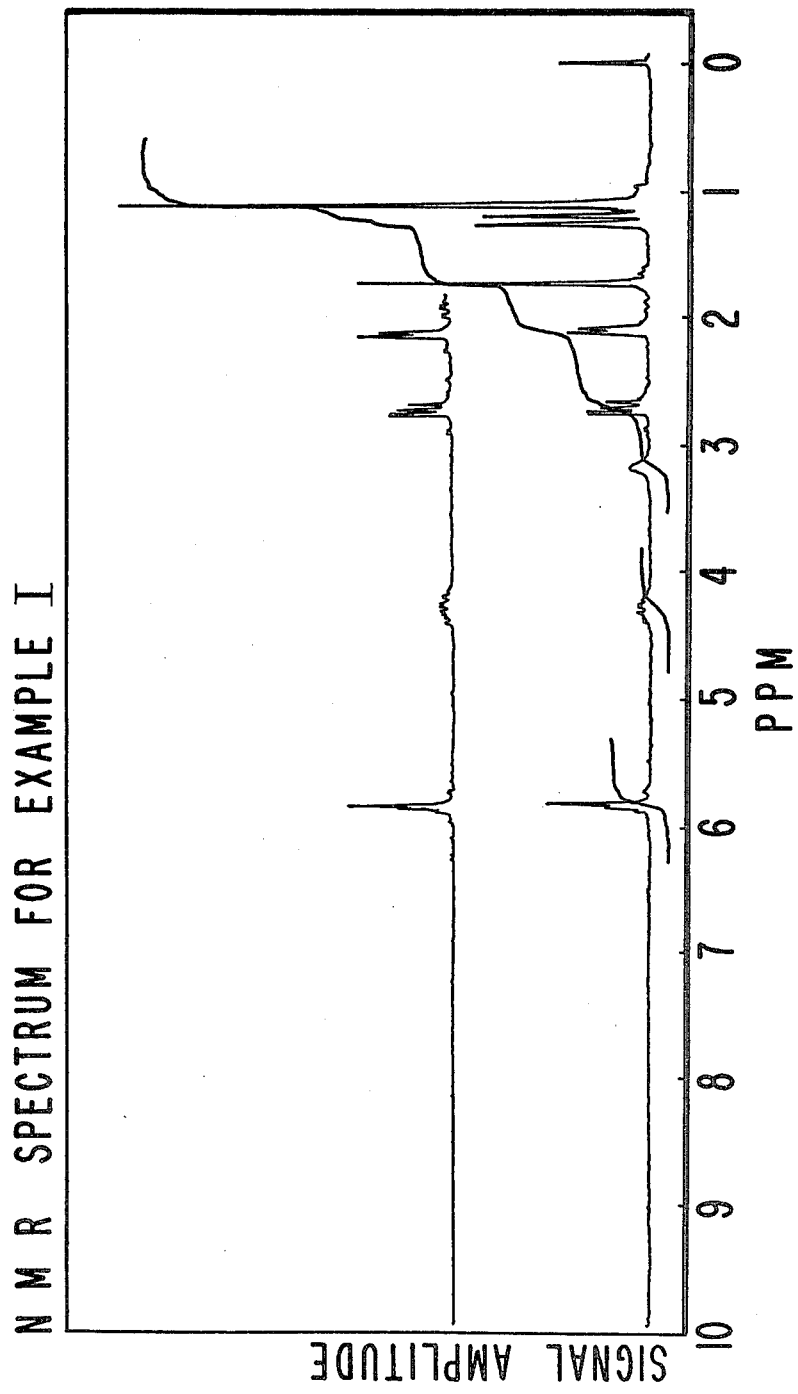
FIG. 1 is the nuclear magnetic resonance (NMR) spectrum for 3-hydroxy-1-(2,6,6-trimethyl-1,3-cyclohexadien-1-yl)-1-butanone produced according to Example IA.

It has now been discovered that novel solid and liquid perfume compositions, colognes and perfumed articles having sweet, honey-like, fruity, grape-like, rose-like, ionone-like, hay-like, and floral aromas with sea-amber and ambergris-like undertones and sweet-floral topnotes as well as novel tobacco and flavoring compositions having sweet, fruity, berry-like, fresh squeezed fruit (apple and grape) juice-like, hay-like and tea-like aromas prior to smoking with sweet, hay/tea aromas in the mainstream on smoking and sweet, tobacco-like and "fresh cigarette pack" aromas in the sidestream on smoking may be provided by 1-(2,6,6-trimethyl-1,3-cyclohexadien-1-yl)-1,3-butanedione which may be represented either by the structure:

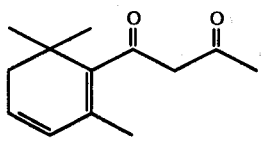

or by the equilibrium relationship:

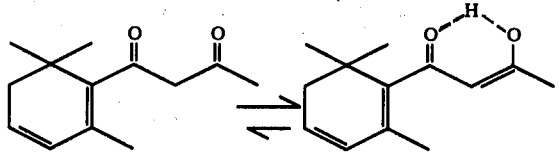

or by the enolate having the structure:

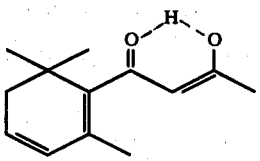

in perfume compositions, perfumed articles, colognes and tobaccos as well as tobacco substitutes.

1-(2,6,6-Trimethyl-1,3-cyclohexadien-1-yl)-1,3-butanedione, useful as indicated supra, may be produced by first reacting 1-acetyl-2,6,6-trimethyl-1,3-cyclohexadiene having the structure:

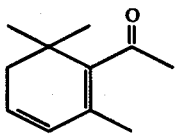

with a methyl magnesium halide having the structure:

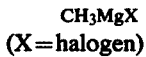

(X=halogen)

wherein X is halogen which may either be chloro, bromo or iodo, thereby forming an organometalic compound having the structure:

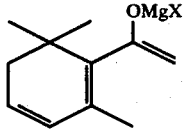

with the evolution of methane. The said organometallic compound having the structure:

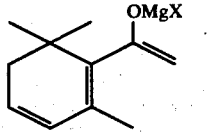

may then be reacted with an acetyl halide having the structure:

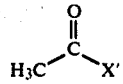

wherein X' is chloro or bromo, thereby forming a second organometalic compound having the structure:

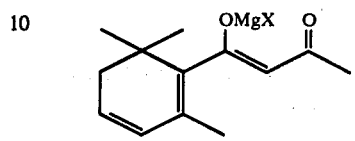

This second organometalic compound is a novel compound. The said second organometalic compound may then be hydrolyzed using dilute acid such as dilute organic acid, e.g. dilute acetic acid or dilute formic acid, or dilute aqueous mineral acid such as dilute hydrochloric acid, dilute sulfuric acid, dilute phosphoric acid or dilute paratoluenesulfonic acid.

The reaction of the methyl magnesium halide with the 1-acetyl-2,6,6-trimethyl-1,3-cyclohexadiene takes place at a temperature in the range of from $-10°$ C. up to $+10°$ C., preferably from $0°-5°$ C. at atmospheric pressure in the presence of an inert anhydrous solvent such as tetrahydrofuran or diethyl ether. The reaction of the first organometalic compound having the structure:

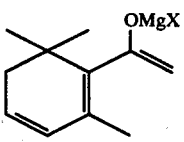

with the acetyl halide having the structure:

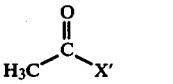

takes place at a temperature in the range of from $0°-30°$ C., preferably at about $20°$ C. It is preferred that the acetyl halide be in slight molar excess with respect to the first organometallic compound having the structure:

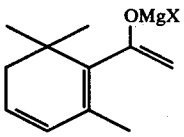

The hydrolysis of the second organometallic compound having the structure:

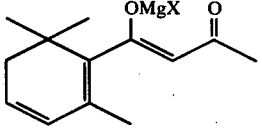

preferably takes place using aqueous acetic acid (in excess) at a temperature of between $5°$ C. and $20°$ C., preferably at about 10° C. at atmospheric pressure. Following the hydrolysis of the second organometallic compound having the structure:

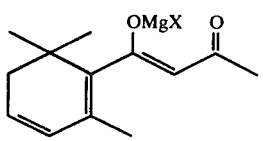

to 1-(2,6,6-trimethyl-1,3-cyclohexadien-1-yl)-1,3-butanedione having the structure:

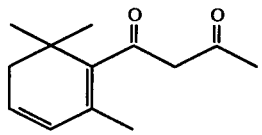

which is actually in equillibrium with the enolate having the structure:

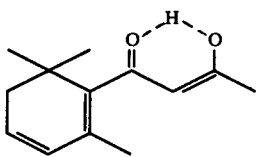

according to the equilibrium:

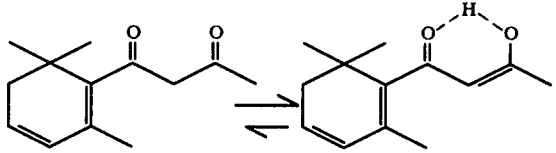

The reaction mass is worked up using standard extraction and distillation procedures.

The aforementioned reaction sequence is illustrated as follows:

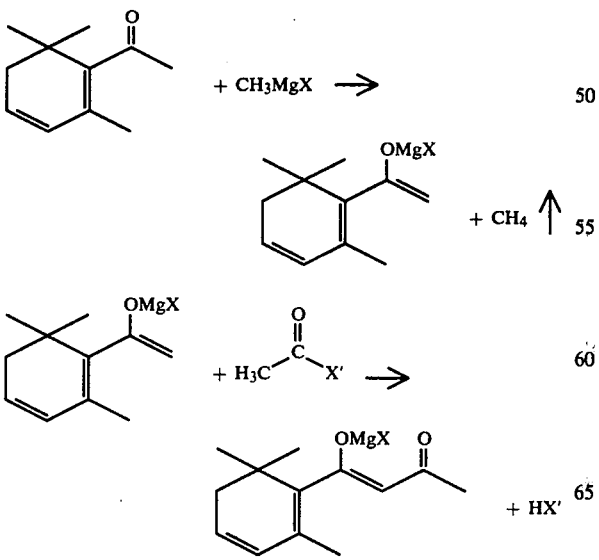

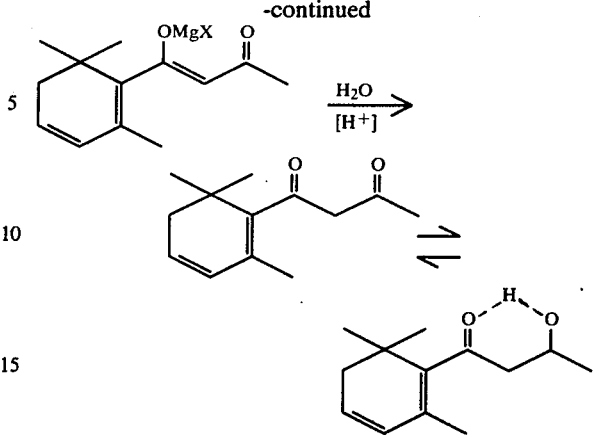

wherein X is halogen selected from the group consisting of chloro, bromo, and iodo, and X' is halogen selected from the group consisting of chloro and bromo.

When it was attempted to oxidize the hydroxyketone having the structure:

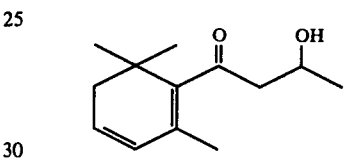

using a standard oxidizing agent, no 1-(2,6,6-trimethyl-1,3-cyclohexadien-1-yl)-1,3-butanedione was formed but β-damascenone having the structure:

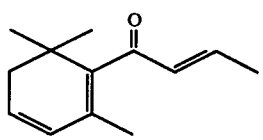

was formed according to the reaction:

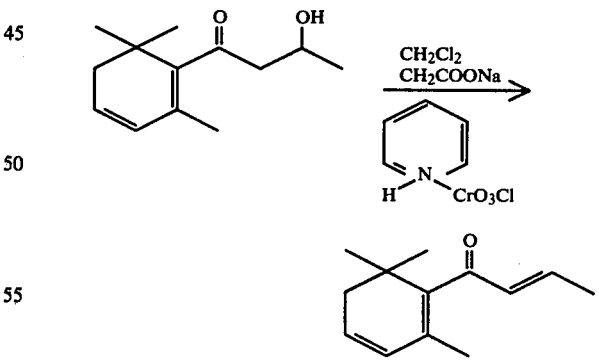

Accordingly, the reaction sequence which was found to be workable is not easily replaceable with an alternative reaction sequence.

According to one aspect of our invention an organoleptically improved smoking tobacco product and additives therefor, as well as methods of making the same which overcome specific problems heretofore encountered in which specific desired sweet, fruity, berry, fresh squeezed fruit (apple and grape) juice-like, hay-like and tea-like aromas prior to smoking and improved body, enhanced tobacco character and sweet, pronounced hay/tea characteristics in the mainstream on smoking and sweet, tobacco-like and "fresh cigarette pack" aromas in the sidestream on smoking, are created or enhanced or modified or augmented and may be readily controlled and maintained at the desired uniform level regardless of variations in the tobacco components of the blend. In particular, low-grade Virginia type tobaccos may be upgraded using the 1-(2,6,6-trimethyl-1,3-cyclohexadien-1-yl)-1,3-butanedione of our invention.

This invention further provides improved tobacco additives and methods whereby various desirable natural aromatic tobacco flavoring characteristics with sweet, floral and fruity notes may be imparted to smoking tobacco products and may be readily varied and controlled to produce the desired uniform flavoring characteristics.

In carrying out this aspect of our invention, we add to smoking tobacco materials or a suitable substitute therefor (e.g. dried lettuce leaves) an aroma and flavor additive containing as an active ingredient the 1-(2,6,6-trimethyl-1,3-cyclohexadien-1-yl)-1,3-butanedione of our invention.

In addition to the 1-(2,6,6-trimethyl-1,3-cyclohexadien-1-yl)-1,3-butanedione of our invention, other flavoring and aroma additives may be added to the smoking tobacco material or substitute therefor either separately or in mixture with the 1-(2,6,6-trimethyl-1,3-cyclohexadien-1-yl)-1,3-butanedione as follows:

I. Synthetic Materials

Beta-ethyl-cinnamaldehyde;
Eugenol;
Dipentene;
β-Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethyl naphtho-(2,1-b)-furan;
4-Hydroxy hexanoic acid, gamma lactone; and
Polyisoprenoid hydrocarbons defined in Example V of U.S. Pat. No. 3,589,372 issued on June 29, 1971.

II. Natural Oils

Celery seed oil;
Coffee extract;
Bergamot oil;
Cocoa extract;
Nutmeg oil; and
Origanum oil.

An aroma and flavoring concentrate containing 1-(2,6,6-trimethyl-1,3-cyclohexadien-1-yl)-1,3-butanedione and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g. lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of 1-(2,6,6-trimethyl-1,3-cyclohexadien-1-yl)-1,3-butanedione to smoking tobacco material is between 50 ppm and 1,500 ppm (0.005%–0.15%) of the active ingredients to the smoking tobacco material. We have further found that satisfactory results are obtained if the proportion by weight of the sum total of 1-(2,6,6-trimethyl-1,3-cyclohexadien-1-yl)-1,3-butanedione used to flavoring material is between 500 and 15,000 ppm (0.05%–1.5%).

Any convenient method for incorporating the 1-(2,6,6-trimethyl-1,3-cyclohexadien-1-yl)-1,3-butanedione into the tobacco product may be employed. Thus, the 1-(2,6,6-trimethyl-1,3-cyclohexadien-1-yl)-1,3-butanedione taken alone or along with other flavoring additives may be dissolved in a suitable solvent such as ethanol, diethyl ether and/or volatile organic solvents, and the resulting solution may either be spread on the cured, cased and blended tobacco material or the tobacco material may be dipped into such solution. Under certain circumstances, a solution of the 1-(2,6,6-trimethyl-1,3-cyclohexadien-1-yl)-1,3-butanedione taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated, and the thus-treated tobacco may be blended with other tobaccos before the ultimate tobacco product is formed. In such cases, the tobacco treated may have the 1-(2,6,6-trimethyl-1,3-cyclohexadien-1-yl)-1,3-butanedione in excess of the amounts or concentrations above indicated so that when blended with other tobaccos, the final product will have the percentage within the indicated range.

In accordance with one specific example of our invention, an aged, cured and shredded domestic Virginia tobacco is spread with a 20% ethyl alcohol solution of 1-(2,6,6-trimethyl-1,3-cyclohexadien-1-yl)-1,3-butanedione in an amount to provide a tobacco composition containing 100 ppm by weight of 1-(2,6,6-trimethyl-1,3-cyclohexadien-1-yl)-1,3-butanedione on a dry basis. Thereafter, the alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as being sweeter with more pronounced hay/tea character with improved body and enhanced tobacco character in the main stream and sweeter, more tobacco-like with a "fresh cigarette pack" aroma in the side stream. Prior to smoking the cigarette has a sweet, fruity, berry-like, fresh squeezed fruit (apple and grape) juice-like, hay-like and tea-like aroma characteristic.

While our invention is particularly useful in the manufacture of smoking tobacco, such as cigarette tobacco, cigar tobacco and pipe tobacco, other tobacco products formed from sheeted tobacco dust or fines may also be used. Likewise, the 1-(2,6,6-trimethyl-1,3-cyclohexadien-1-yl)-1,3-butanedione of our invention can be incorporated with materials such as filter tip materials, seam paste, packaging materials and the like which are used along with tobacco to form a product adapted for smoking. Furthermore, the 1-(2,6,6-trimethyl-1,3-cyclohexadien-1-yl)-1,3-butanedione can be added to certain tobacco substitutes of natural or synthetic origin (e.g. dried lettuce leaves) and, accordingly, by the term "tobacco" as used throughout this specification is meant any composition intended for human consumption by smoking or otherwise, whether composed of tobacco plant parts or substitute materials or both.

The 1-(2,6,6-trimethyl-1,3-cyclohexadien-1-yl)-1,3-butanedione and one or more auxiliary perfume ingredients, including, for example, alcohols, aldehydes, ketones other than 1-(2,6,6-trimethyl-1,3-cyclohexadien-1-yl)-1,3-butanedione, nitriles, esters, cyclic esters (lactones), dialkyl ethers, alkyl alkenyl ethers, thioethers, thiols, carboxylic acids and natural essential oils may be admixed so that the combined odors of the individual components produce a pleasant and desired fragrance, particularly and preferably in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materails.

In perfume compositions, it is the individual components which contribute to their particular olfactory characteristics, however, the over-all sensory effect of the perfume composition will be at least the sum total of the effects of each of the ingredients. Thus the 1-(2,6,6-trimethyl-1,3-cyclohexadien-1-yl)-1,3-butanedione can be used to alter, modify or enhance the aroma characteristics of a perfume composition, for example, by utilizing or moderating the olfactory reaction contributed by another ingredient in the composition.

The amount of 1-(2,6,6-trimethyl-1,3-cyclohexadien-1-yl)-1,3-butanedione of our invention which will be effective in perfume compositions as well as in perfumed articles and colognes depends on many factors, including the other ingredients, their amounts and the effects which are desired. It has been found that perfume compositions containing as little as 0.01% of 1-(2,6,6-trimethyl-1,3-cyclohexadien-1-yl)-1,3-butanedione or even less (e.g. 0.005%) can be used to impart a sweet, honey-like, fruity, grape-like, rose-like, ionone-like, hay-like and floral aroma with sea-amber, and ambergris-like undertones and sweet-floral topnotes to soaps, cosmetics or other products. The amount employed can range up to 70% of the fragrance components and will depend on considerations of cost, nature of the end product, the effect desired on the finished product and the particular fragrance sought.

The 1-(2,6,6-trimethyl-1,3-cyclohexadien-1-yl)-1,3-butanedione of our invention is useful (taken alone or together with other ingredients in perfume compositions) as (an) olfactory component(s) in detergents and soaps, space odorants and deodorants, perfumes, colognes, toilet water, bath preparations such as lacquers, brilliatines, pomades and shampoos; cosmetic preparations, such as creams, deodorants, hand lotions and sun screens; powders, such as talcs, dusting powders, face powders and the like. When used as (an) olfactory component(s) as little as 1% of 1-(2,6,6-trimethyl-1,3-cyclohexadien-1-yl)-1,3-butanedione will suffice to impart an intense floral note to rose formulations. Generally, no more than 3% of 1-(2,6,6-trimethyl-1,3-cyclohexadien-1-yl)-1,3-butanedione based on the ultimate end product, is required in the perfume composition.

In addition, the perfume composition or fragrance composition of our invention can contain a vehicle, or carrier for the 1-(2,6,6-trimethyl-1,3-cyclohexadien-1-yl)-1,3-butanedione. The vehicle can be a liquid such as a non-toxic alcohol, a non-toxic glycol, or the like. The carrier can also be an absorbent solid, such as a gum (e.g. gum arabic) or components for encapsulating the composition (such as gelatin).

It will thus be apparent that the 1-(2,6,6-trimethyl-1,3-cyclohexadien-1-yl)-1,3-butanedione of our invention can be utilized to augment, alter, modify or enhance sensory properties, particularly organoleptic properties, such as flavor(s) and/or fragrance(s) of a wide variety of consumable materials.

Example I, following, serves to illustrate the unworkability of a process which was at first thought to have the ability to yield 1-(2,6,6-trimethyl-1,3-cyclohexadien-1-yl)-1,3-butanedione. Example II, following, serves to illustrate the process for specifically producing 1-(2,6,6-trimethyl-1,3-cyclohexadien-1-yl)-1,3-butanedione useful in our invention. Examples III and the following examples serve to illustrate the utilities of the 1-(2,6,6-trimethyl-1,3-cyclohexadien-1-yl)-1,3-butanedione of our invention.

It will be understood that these examples are illustrative, and the invention is to be considered restricted thereto only as indicated in the appended claims.

All parts and percentages given herein are by weight unless otherwise specified.

EXAMPLE IA

PREPARATION OF 3-HYDROXY-1-(2,6,6-TRIMETHYL-1,3-CYCLOHEXADIEN-1-YL)-1-BUTANONE

Reactions:

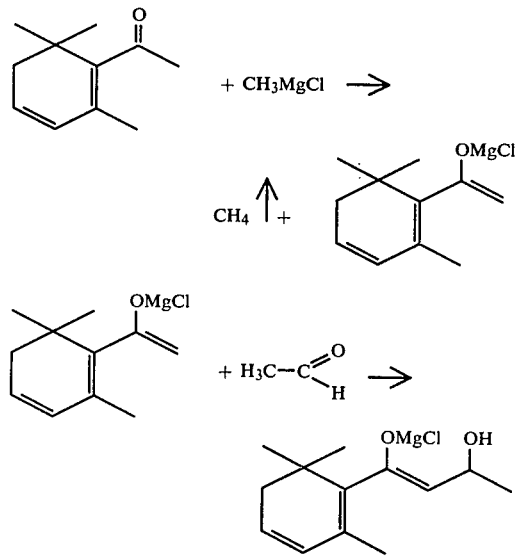

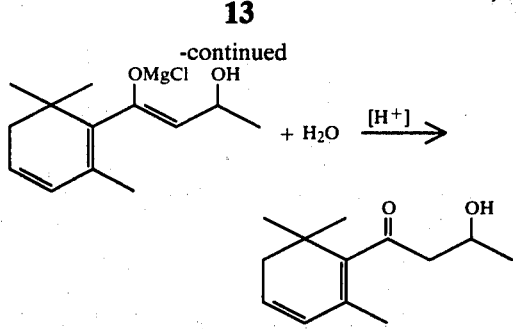

Into a 2-liter reaction flask equipped with a mechanical stirrer, cooling bath, 250 ml addition funnel, nitrogen purge, water-cooled condenser, gas bubbler and thermometer, is placed 427 ml (1.3 moles) of a 3-molar solution of methyl magnesium chloride in tetrahydrofuran. 200 Grams (1.22 moles) of 2,6,6-trimethyl-1-acetylcyclohexa-1,3-diene are added dropwise from the addition funnel at a rate sufficient to produce methane. Cooling is applied as necessary to maintain the reaction temperature between 30° and 35° C. Following completion of the addition of the 2,6,6-trimethyl-1-acetylcyclohexa-1,3-diene, the reaction mass is stirred until no further methane is evolved. The reaction mass is then cooled to a temperature in the range of from 0° C. to 5° C., and 59 grams of acetaldehyde is added dropwise with stirring while maintaining the reaction mass temperature at about 10° C. The reaction is slightly exothermic. 15 Minutes after the completion of the addition of acetaldehyde, acetic acid is added dropwise while maintaining the temperature of the reaction mass at about 10° C. Following the addition of acetic acid, the reaction mass is permitted to reach room temperature. The reaction mass is then washed into a separatory funnel with water to dissolve the salt therein. The resulting organic layer is washed with saturated sodium chloride, saturated sodium bicarbonate, and then saturated sodium chloride. The washed organic layer is then dried over anhydrous magnesium sulfate and concentrated on a rotovap yielding 256 grams of residue.

The resulting hydroxyketone having the structure:

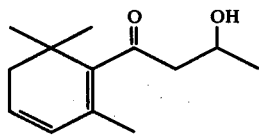

is distilled under vacuum in order to separate it from other impurities. 70 Grams of the distilled material is combined with 80 grams of Primol ® and distilled under 0.25–0.60 mm Hg pressure into nine fractions. The distillation data is as follows:

| Vapor Temp. | Liquid Temp. | Weight of Fraction | Fraction # |
|---|---|---|---|
| 22°–40.5° | 24°–85° | 3.96 | 1 |
| 40.0 | 94 | 6.50 | 2 |
| 44 | 105 | 2.90 | 3 |
| 88 | 114 | 4.24 | 4 |
| 89.5 | 116.5 | 4.50 | 5 |
| 90.75 | 120.0 | 8.01 | 6 |
| 93.0 | 128.0 | 8.34 | 7 |
| 88.5 | 147.0 | 7.93 | 8 |
| 87.0 | 147.0 | 3.51 | 9 |

Fraction #6 is found to be substantially pure and is submitted for mass spectral, NMR, IR and UV analyses.

Figure 2:
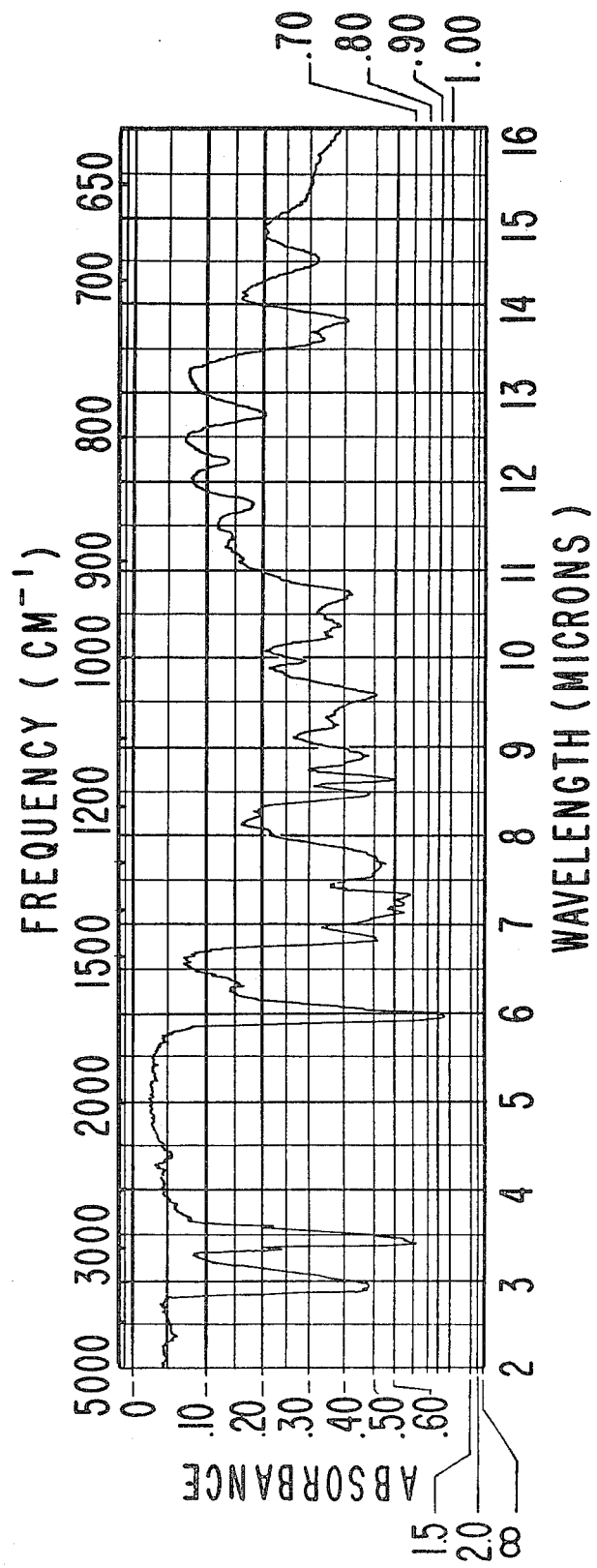
FIG. 2 is the infrared (IR) spectrum for 3-hydroxy-1-(2,6,6-trimethyl-1,3-cyclohexadien-1-yl)-1-butanone produced according to Example IA.

The NMR spectrum is set forth in FIG. 1. The infrared spectrum is set forth in FIG. 2. The mass spectrum is set forth in FIG. 3. The ultraviolet absorption spectrum (using a methanol solvent) is set forth in FIG. 4. $\lambda_{max}=277$ nm. $E_{1\ cm}^{1\%}=176.65$ in methyl alcohol. The NMR analysis is as follows:

| Chem. Shift | Signal Type | Assignment | Quant. |
|---|---|---|---|
| 1.10 | S | 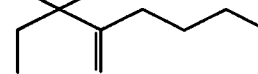 | 6H |
| 1.23 | d | 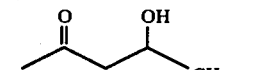 | 3H |
| 1.74 | S | 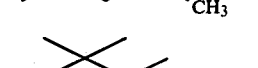 | 3H |
| 2.11 | d | 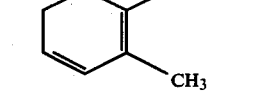 | 2H |
| 2.71 | m |  | 2H |
| 3.20 | Broad | 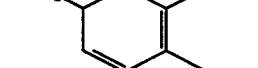 | 1H |
| 4.30 | M | 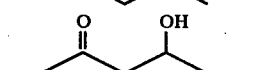 | 1H |
| 5.82 | M | 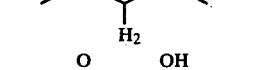 | 2H |

The infrared analysis is as follows:

| | |
|---|---|
| 3400–3500 cm$^{-1}$ | strong |
| 3000 | moderate |
| 2950 | strong |
| 2800 | moderate |
| 1680 | strong |
| 1580 | weak |
| 1460 | strong |
| 1360–1400 | strong |
| 1280–1330 | strong |
| 1185 | moderate |
| 1160 | strong |
| 1125 | moderate |
| 1040 | moderate |
| 1005 | moderate |
| 935–980 | moderate |
| 850 | weak |
| 820 | weak |
| 783 | moderate |
| 723–737 | moderate |
| 690 | moderate |

The mass spectral analysis is as follows:

| M/E | Relative Intensity |
|---|---|
| 43 | 100 |
| 69 | 18 |
| 77 | 13 |
| 79 | 11 |
| 91 | 18 |
| 105 | 30 |
| 121 | 81 |
| 122 | 10 |
| 149 | 9 |
| 164 | 12 |
| 190 | 2 |
| 208p | 1 |

EXAMPLE IB
ABORTED RUN

Attempted synthesis of 1-(2,6,6-trimethyl-1,3-cyclohexadien-1-yl)-1,3-butanedione (actual production of "β-Damascenone")

Reaction:

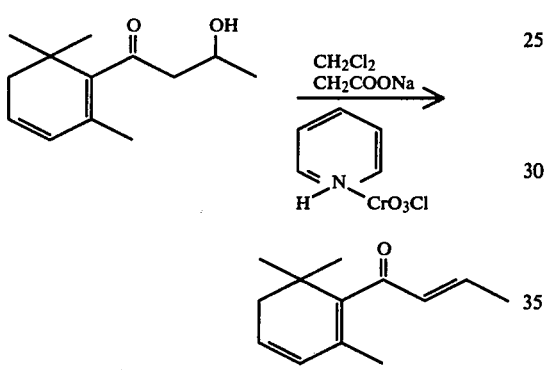

It was attempted to oxidize the keto alcohol, the product of the process of Example IA to a diketone according to the procedure of Cory and Suggs, Tetrahedron Letters No. 31, pages 2647–2650 (1975). The Cory and Suggs reagent is pyridinium chlorochromate. However, βDamascenone, having the structure:

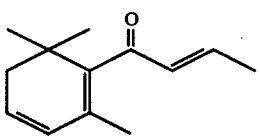

was produced rather than 1-(2,6,6-trimethyl-1,3-cyclohexadien-1-yl)-1,3-butanedione, having the structure:

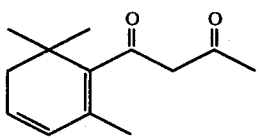

Into a 250 ml three-necked, round-bottom flask equipped with water cooled condenser and magnetic stirrer is placed 12.30 grams of pyridinium chlorochromate slurried in 100 ml methylene dichloride (CH₂Cl₂). The product of the process of Example IA having the structure:

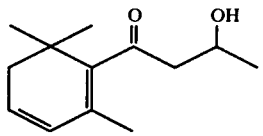

(7.93 grams [0.038 moles]) is dissolved in 20 ml methylene dichloride and is added to the reaction mass with stirring. The resulting mixture is permitted to stir at room temperature for a period of two hours during which time the color of the solution changes from orange to black.

The reaction mass is removed from the reaction flask using 100 ml diethyl ether. The reaction flask is then washed three times with diethyl ether leaving a black "tar-like" substance behind. The organic layer is then washed twice with sodium bicarbonate and saturated sodium chloride solution, and is then concentrated on a rotovap yielding 7.06 grams of crude material. A 5 microliter injection is made on a 20' SE-30 GLC column and run from 100°–225° C. at 4° C./min. The major peak is analyzed using infrared analysis and found to be β-Damascenone having the structure:

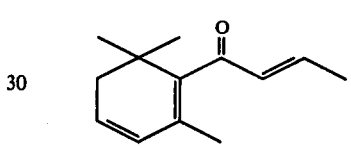

EXAMPLE II

PREPARATION OF 1-(2,6,6-TRIMETHYL-1,3-CYCLOHEXADIEN-1,3-BUTANEDIONE

Reaction:

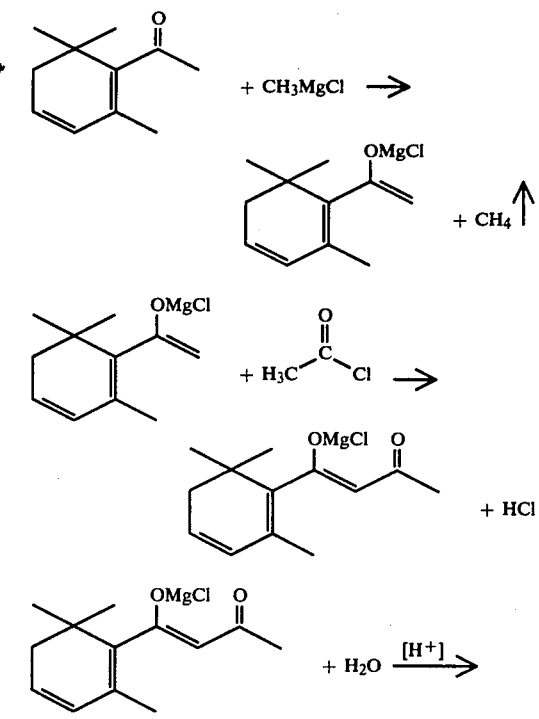

-continued

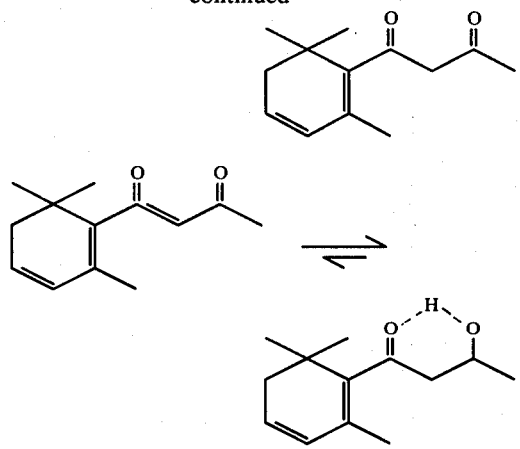

Into a 250 ml three-necked, round-bottom flask equipped with a mechanical stirrer, an immersion thermometer, a nitrogen purge, a dry ice/isopropanol cooling bath, a 125 ml addition funnel and a water-cooled condenser with gas bubbler, is placed 42.7 ml of a tetrahydrofuran solution of methyl magnesium chloride (3 molar). The methyl magnesium chloride/THF solution is chilled to 0°–5° C. with stirring, and 20 grams (0.122 moles) of acetyl-2,6,6-trimethyl-1,3-cyclohexadiene is added dropwise over a minute period. Following completion of the addition, the reaction mass is stirred at about 20° C. until no further methane is observed to evolve (approximately a 30 minute period). The reaction mass is then chilled to 0° C. and 10.14 grams (0.13 moles) of freshly distilled acetyl chloride is added dropwise over a 20 minute period. Following the addition of the acetyl chloride, the reaction mass is stirred at a temperature of 20° C. for 15 minutes and then once more chilled to 10° C., and a solution of 8.1 grams of acetic acid in 10 ml water is added dropwise during a 5 minute period. Following the addition of the acid, water is added to dissolve salts, and the reaction mass is transferred to a separatory funnel. Diethyl ether is added, and the ether layer is separated and washed twice with saturated sodium bicarbonate solution and then twice with saturated sodium chloride solution; dried and concentrated in vacuo. The concentrate is then analyzed using GLC (Conditions: 20′×¼″ 5% SE-30 column). NMR, IR and mass spectral data confirm that the last eluting major peak is 1-(2,6,6-trimethyl-1,3-cyclohexadien-1-yl)-1,3-butanedione. The residue is then submitted to fractional distillation after adding thereto 50 grams Primol ®. The fractional distillation is carried out on a 14″×¾″ Vigreaux column yielding the following fractions:

| Fraction No. | Vapor Temp. | Liquid Temp. | Vacuum (mm Hg) | Weight (grams) |
|---|---|---|---|---|
| 1 | 23–39 | 24–114.5 | 0.175 | 7.81 |
| 2 | 67 | 143 | 0.02 | 5.92 |
| 3 | 61 | 194 | 0.28 | 3.90 |
| 4 | 94 | 225 | 0.25 | 5.56 |

Fraction 3 contains 95.4% 1-(2,6,6-trimethyl-1,3-cyclohexadien-1-yl)-1,3-butanedione.

NMR spectrum for 1-(2,6,6-trimethyl-1,3-cyclohexadien-1-yl)-1,3-butanedione of fraction 3 is set forth in FIG. 5. The IR spectrum for 1-(2,6,6-trimethyl-1,3-cyclohexadien-1-yl)-1,3-butanedione of fraction 3 is set forth in FIG. 6. The UV absorption curve for 1-(2,6,6-trimethyl-1,3-cyclohexadien-1-yl)-1,3-butanedione of fraction 3 is set forth in FIG. 7 ($E_1 \; cm^{1\%} = 473.04$; $\lambda_{max} = 284$ nm).

The infrared analysis (in carbontetrachloride solution) is as follows:
1000 cm$^{-1}$
1160
1175
1225
1250
1295
1360
1440
1600 (broad)
2920
2970

The NMR analysis (in C Cl$_3$ solution) is as follows:

| ppm | interpretation | |
|---|---|---|
| 1.10 (s) | gem dimethyl protons | 6H |
| 1.75 (s) | $CH_3-C=C-C-$<br>$\phantom{CH_3-C=C-}\|\|$<br>$\phantom{CH_3-C=C-}O$ | 3H |
| 2.30 (s) | $CH_3-C=C-$<br>$\phantom{CH_3-C=C}\|$<br>$\phantom{CH_3-C=C}O-$ | 3H |
| 5.45 (s) | olefinic proton | 1H |
| 5.80 (s) | olefinic protons | 2H |
| 15.67 (broad) | bonded H | |

The mass spectral analysis for 1-(2,6,6-trimethyl-1,3-cyclohexadien-1-yl)-1,3-butanedione is as follows:

| M/E | Relative Intensity |
|---|---|
| 39 | 30 |
| 41 | 24 |
| 43 | 100 |
| 77 | 10 |
| 85 | 77 |
| 91 | 11 |
| 105 | 11 |
| 121 | 21 |
| 191 | 11 |
| 206p | 12 |

EXAMPLE III

Rose Formulation

To demonstrate the use of 1-(2,6,6-trimethyl-1,3-cyclohexadien-1-yl)-1,3-butanedione in a rose formulation, the following formula is provided:

| Ingredient | Parts by Weight |
|---|---|
| Phenylethyl alcohol | 200 |
| Geraniol | 400 |
| Trichloromethylphenyl carbinyl acetate | 20 |
| Phenylethyl acetate | 60 |
| Undecylenic aldehyde (10% in diethyl phthalate) | 5 |
| n-Nonyl aldehyde (10% in diethyl phthalate) | 2 |
| Musk ketone | 10 |
| Musk ambrette | 10 |
| Eugenol phenyl acetate | 20 |
| Citronellol | 100 |
| Vanillin (10% in diethyl phthalate) | 6 |
| Eugenol | 30 |
| Citronellyl formate | 30 |
| Geranyl acetate | 10 |

-continued

| Ingredient | Parts by Weight |
| --- | --- |
| Linalool | 40 |
| Geranyl phenyl acetate | 50 |
| Cis beta, γ-hexenyl acetate | 2 |
| 1-(2,5,5-trimethyl-1,3-cyclohexadien-1-yl)-1,3-butanedione prepared according to Example II | 5 |

The addition of 0.5% of 1-(2,6,6-trimethyl-1,3-cyclohexadien-1-yl)-1,3-butanedione lends a great deal of strength and character to the rose fragrance. It contributes great floralcy and the heady natural sweetness of the red rose flower together with honey-like, fruity, grape-like, and hay-like nuances and sea-amber undertones with sweet-floral topnotes.

At lower concentrations (0.01%) its contribution is more subtle; however, it still gives an interesting natural effect with the ambergris-like undertone.

This product may normally be used from approximately 0.01% to 10% in perfume compositions. For special effects, however, higher concentrations (50% plus) can be used.

EXAMPLE IV

Preparation of a Soap Composition

One hundred grams of soap chips are produced according to Example V of U.S. Pat. No. 4,058,487 issued on Nov. 15, 1977, as follows:

The sodium salt of an equal mixture of $C_{10}/C_{14}$ alkane sulfonate (95% active), 40 pounds, is dissolved in a mixture of 80 pounds of anhydrous isopropanol and 125 pounds of deionized water at 150° F. In this mixture is dissolved 10 pounds of partially hydrogenated cocoanut oil fatty acids and 15 pounds of sodium mono-$C_{14}$ alkyl maleate, and the pH of this solution is adjusted to 6.0 by the addition of a small amount of 50% aqueous solution of sodium hydroxide. The isopropanol is distilled off, and the remaining aqueous solution is drum dried. The resulting solid actives are then blended in a chip mixture with 10 pounds water, 0.2 pounds titanium hydroxide and 0.7 pounds of the material, 1-(2,6,6-trimethyl-1,3-cyclohexadien-1-yl)-1,3-butanedione. The chips are then plotted into logs, cut to size and finally stamped into bars having a pH of approximately 6.9.

The perfumed soap manifests an excellent rose character with excellent sweet, honey-like, fruity, hay-like and floral nuances with a sea-amber and ambergris-like undertone and sweet-floral topnotes.

EXAMPLE V

Preparation of a Detergent Composition

A total of 100 grams of a detergent powder prepared according to U.S. Pat. No. 4,058,472 and containing 5% by weight of the sodium salts of a mixture of sulfonated $C_{14}-C_{18}$ alkyl catechol as a surface active component, the mixture being 60 parts by weight of mono-$C_{14}-C_{18}$ alkyl catechol and 40 parts by weight of di-$C_{14}-C_{18}$ alkyl catechol, 35% of sodium tetrapyrophosphate, 30% of sodium silicate, 20% of sodium carbonate, 3% of sodium carboxymethyl cellulose and 7% of starch is mixed with 0.15 grams of 1-(2,6,6-trimethyl-1,3-cyclohexadien-1-yl)-1,3-butanedione of Example II until a substantially homogeneous composition is obtained. This composition has an excellent rose aroma with sweet, honey-like, fruity, grape-like, hay-like and floral nuances and a sea-amber/ambergris-like undertone with sweet-floral topnotes.

EXAMPLE VI

Tobacco Formulation

A tobacco mixture is produced by admixing the following ingredients:

| Ingredient | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at a rate of 0.1% to all of the cigarettes produced using the above tobacco formulation. Half of the cigarettes are then treated with 50 or 150 ppm of 1-(2,6,6-trimethyl-1,3-cyclohexadien-1-yl)-1,3-butanedione produced according to the process of Example II. The control cigarettes not containing the 1-(2,6,6-trimethyl-1,3-cyclohexadien-1-yl)-1,3-butanedione and the experimental cigarettes which contain the 1-(2,6,6-trimethyl-1,3-cyclohexadien-1-yl)-1,3-butanedione produced according to the process of Example II are evaluated by paired comparison, and the results are as follows.

The experimental cigarettes are found, on smoking, to have improved "body," enhanced tobacco character, to be sweeter, and to have more pronounced hay/tea character in the mainstream. The experimental cigarettes are also found, on smoking, to be sweeter, more tobacco-like, having a "fresh cigarette pack" aroma in the sidestream.

The tobacco of the experimental cigarettes, prior to smoking, has sweet, fruity, berry-like, fresh squeezed fruit (apple and grape) juice-like, hay-like and tea-like aroma characteristics.

All cigarettes are evaluated for smoke flavor with a 20 mm cellulose acetate filter.

The 1-(2,6,6-trimethyl-1,3-cyclohexadien-1-yl)-1,3-butanedione produced according to Example II enhances the tobacco-like taste and aroma of the blended cigarette imparting to it sweet, natural tobacco "fresh cigarette pack" notes as well as hay/tea notes.

EXAMPLE VII

Preparation of a Cosmetic-Powder Composition

A cosmetic powder is prepared by mixing in a ball mill, 100 grams of talcum powder with 0.25 grams of 1-(2,6,6-trimethyl-1,3-cyclohexadien-1-yl)-1,3-butanedione prepared according to Example II. It has an excellent sweet, honey-like, fruity, grape-like, rose-like, ionone-like, hay-like and floral-like aroma with a sea-amber/ambergris-like undertone and sweet-floral topnotes.

EXAMPLE VIII

Perfumed Liquid Detergent

Concentrated liquid detergents with sweet, honey-like, fruity, grape-like, rose-like, ionone-like, hay-like and floral aromas and sea-amber/ambergris-like undertones and sweet-floral topnotes are prepared by adding 0.10%, 0.15% and 0.20% of 1-(2,6,6-trimethyl-1,3-cyclohexadien-1-yl)-1,3-butanedione prepared according to Example II. They are prepared by adding and homogeneously mixing the appropriate quantity of 1-(2,6,6-trimethyl-1,3-cyclohexadien-1-yl)-1,3-butanedione in the liquid detergent. The detergents all possess sweet, honey-like, fruity, grape-like, rose-like, ionone-like, hay-like and floral aromas with sea-amber/ambergris-like undertones, the intensity increasing with greater concentrations of 1-(2,6,6-trimethyl-1,3-cyclohexadien-1-yl)-1,3-butanedione.

EXAMPLE IX

Preparation of a Cologne and Handkerchief Perfume 1-(2,6,6-Trimethyl-1,3-cyclohexadien-1-yl)-1,3-butanedione prepared according to Example II is incorporated into colognes of several strengths at concentrations of 2.0%, 2.5%, 3.0%, 3.5%, 4.0%, and 5.0% in 85% aqueous ethanol; and into several concentrations of handkerchief perfumes at the rate of 15%, 20% and 25% (in 95% aqueous ethanol). Distinct and definite sweet, honey-like, fruity, grape-like, rose-like, ionone-like, hay-like and floral aromas with sea-amber/ambergris-like undertones and sweet-floral topnotes are imparted to the colognes and to the handkerchief perfumes of the several concentrations set forth above.

EXAMPLE X

Preparation of a Cologne and Handkerchief Perfume

The composition of Example III is incorporated into colognes of several concentrations, 2.0%, 2.5%, 3.0%, 3.5%, 4.0% and 5.0%, in 85% aqueous ethanol; and into handkerchief perfumes at concentrations of 15%, 20% and 25% (in 95% aqueous ethanol). The use of the 1-(2,6,6-trimethyl-1,3-cyclohexadien-1-yl)-1,3-butanedione in the composition of Example III affords a distinct and definite strong rose aroma with sweet, fruity, hay-like, and floral aromas and sea-amber/ambergris-like undertones with sweet-floral topnotes to the handkerchief perfumes and the colognes at all of the concentrations set forth above.

EXAMPLE XI

Preparation of a Soap Composition

One hundred grams of soap chips are intimately admixed with one gram of 1-(2,6,6-trimethyl-1,3-cyclohexadien-1-yl)-1,3-butanedione until a substantially homogeneous composition is obtained. The perfumed soap composition manifests an excellent sweet, honey-like, fruity, grape-like, rose-like, ionone-like, hay-like and floral aroma with sea-amber/ambergris-like undertones and sweet-floral topnotes.

EXAMPLE XII

Preparation of a Detergent Composition

A total of 100 grams of a detergent powder is intimately admixed with 0.15 grams of 1-(2,6,6-trimethyl-1,3-cyclohexadien-1-yl)-1,3-butanedione prepared according to Example II until a substantially homogeneous composition is obtained. This composition has an excellent sweet, honey-like, fruity, grape-like, rose-like, ionone-like, hay-like and floral aroma with sea-amber/ambergris-like undertones and sweet-floral topnotes.

What is claimed is:

1. Substantially pure 1-(2,6,6-Trimethyl-1,3-cyclohexadien-1-yl)-1,3-butanedione, having the structure:

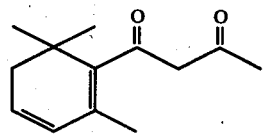

2. An equilibrium mixture consisting essentially of substantially pure compounds having the structures:

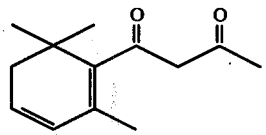

and

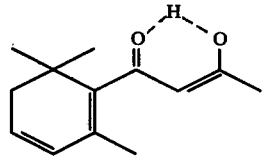

* * * * *